(12) United States Patent
Zinser et al.

(10) Patent No.: US 8,076,513 B2
(45) Date of Patent: Dec. 13, 2011

(54) METHODS FOR THE PREPARATION OF N-ISOBUTYL-N-(2-HYDROXY-3-AMINO-4-PHENYLBUTYL)-P-NITROBENZENESULFONYLAMIDE DERIVATIVES

(75) Inventors: Hartmut Burghard Zinser, Schaffhausen (CH); Peter Hermann Hölzle, Schaffhausen (CH)

(73) Assignee: Tibotec Pharmaceuticals Ltd., Little Island (IE)

( * ) Notice: Subject to any disclaimer, the term of this patent is extended or adjusted under 35 U.S.C. 154(b) by 227 days.

(21) Appl. No.: 12/597,088

(22) PCT Filed: Apr. 25, 2008

(86) PCT No.: PCT/EP2008/055042
§ 371 (c)(1),
(2), (4) Date: Oct. 22, 2009

(87) PCT Pub. No.: WO2008/132154
PCT Pub. Date: Nov. 6, 2008

(65) Prior Publication Data
US 2010/0121094 A1    May 13, 2010

(30) Foreign Application Priority Data

Apr. 27, 2007  (EP) .................................... 07107177

(51) Int. Cl.
C07C 303/38  (2006.01)
C07C 311/18  (2006.01)
(52) U.S. Cl. .......................................... 564/87; 549/464
(58) Field of Classification Search .......... None
See application file for complete search history.

(56) References Cited

U.S. PATENT DOCUMENTS

| | | | |
|---|---|---|---|
| 6,867,321 B2 | 3/2005 | Ikemoto et al. | |
| 2004/0162340 A1 | 8/2004 | Ikemoto et al. | |

FOREIGN PATENT DOCUMENTS

| | | |
|---|---|---|
| EP | 0715618 B1 | 12/1998 |
| EP | 0754669 B1 | 10/2001 |
| EP | 0810209 B1 | 6/2002 |
| EP | 0885887 B1 | 5/2003 |
| EP | 1081133 B1 | 3/2004 |
| EP | 1029856 B1 | 6/2004 |
| EP | 1215209 B1 | 8/2004 |
| EP | 1067125 B1 | 7/2006 |
| WO | WO 95/06030 A1 | 3/1995 |
| WO | WO 97/18205 A1 | 5/1997 |
| WO | WO 99/65870 A2 | 12/1999 |
| WO | WO 99/67254 A2 | 12/1999 |
| WO | WO 99/67417 A2 | 12/1999 |
| WO | WO 00/47551 A2 | 8/2000 |
| WO | WO 00/76961 A1 | 12/2000 |
| WO | WO 01/46120 A1 | 6/2001 |
| WO | WO 03/022853 A1 | 3/2003 |
| WO | WO 2004/033462 A2 | 4/2004 |
| WO | WO 2005/063770 A1 | 7/2005 |
| WO | WO 2005/095410 A1 | 10/2005 |

OTHER PUBLICATIONS

Flosi, W., et al. "Discovery of Imidazolidine-2,4-Dione-Linked HIV Protease Inhibitors With Activity Against Lopinavir-Resistant Mutant HIV", Bioorganic & Medical Chemistry 14 (2006) pp. 6695-6712.
Ghosh, A., et al. Steroselective Photochemical 1,3-Dioxolane Addition to 5-Alkoxyrnethyl-2(5H)-Furanone: Synthesis of Bis-Tetrahydrofuranyl Ligand for HIV Protease Inhibitor UIC-94017 9TMC-114), JOC 2004, v69, p. 7822.
March, Jerry, "Advanced Organic Chemistry", ($3^{rd}$ Ed. 1985), pp. 368-369.
McManus, Samuel, et al., "The Synthesis of Aminoalcohols From Epoxides and Ammonia", Synthetic Communications, (1973), pp. 177-180, vol.-issue 3(3).
International Search Report (date of mailing Aug. 22, 2008) for corresponding Patent Application No. PCT/EP2008/055042.

*Primary Examiner* — Daniel Sullivan
*Assistant Examiner* — Yevegeny Valenrod

(57) ABSTRACT

A process for the preparation of N-isobutyl-N-(2-hydroxy-3-amino-4-phenylbutyl)-p-nitrobenzenesulfonylamide derivatives in which a (1-benzyl-2-hydroxy-3-isobutylamino-propyl)-carbamic acid derivative is reacted with a p-nitrophenylsulfonyl halide to provide the desired product in a high yield and degree of purity.

9 Claims, No Drawings

METHODS FOR THE PREPARATION OF N-ISOBUTYL-N-(2-HYDROXY-3-AMINO-4-PHENYLBUTYL)-P-NITROBENZENESULFONYLAMIDE DERIVATIVES

CROSS REFERENCE TO RELATED APPLICATIONS

This application is a national stage application of Patent Application No. PCT/EP2008/055042, filed Apr. 25, 2008, which application claims priority from EPO Patent Application No. 07107177.3, filed Apr. 27, 2007 all of which are hereby incorporated by reference in their entirety.

The present invention relates to methods for the preparation of N-isobutyl-N-(2-hydroxy-3-amino-4-phenylbutyl)-p-nitrobenzenesulfonylamide derivatives and especially 3N-protected derivatives.

N-isoButyl-N-(2-hydroxy-3-amino-4-phenylbutyl)-p-nitrobenzenesulfonylamide derivatives and especially 3N-protected derivatives such as the tert-butyloxycarbonyl derivative are important intermediates in the synthesis of retroviral protease inhibitors such as those described in WO 99/65870, WO 99/67254, WO 99/67417, WO00/47551, WO 00/76961, WO 05/063770 and EP 0 715 618. Said publications are herein incorporated by reference. One such protease inhibitor which has been approved in the USA for human clinical use for the treatment of retroviral infections and having the above structural moiety is the compound having the USAN approved name darunavir with the chemical name [(1S,2R)-3-[[(4-aminophenyl)sulfonyl](2-methylpropyl)-amino]-2-hydroxy-1-(phenylmethyl)propyl]-carbamic acid (3R,3aS,6aR) hexahydrofuro[2,3-b]furan-3-yl ester and the structure of formula (A):

(A)

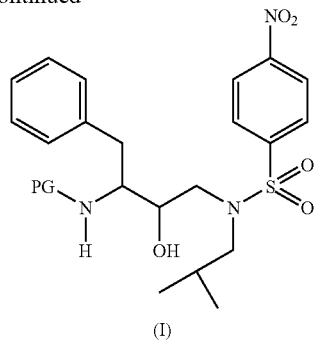

N(3)-Protected derivatives of N-isobutyl-N-(2-hydroxy-3-amino-4-phenylbutyl)-p-nitrobenzenesulfonylamide derivatives of formula I below may be prepared by the reaction of a compound of formula (II) with a p-nitrophenylsulfonyl halide of formula (III) as shown in the reaction scheme below:

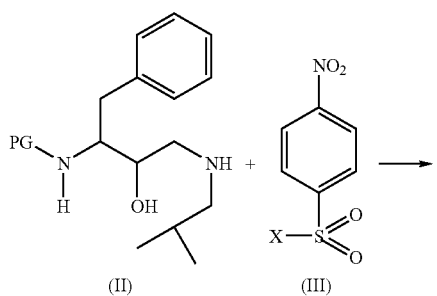

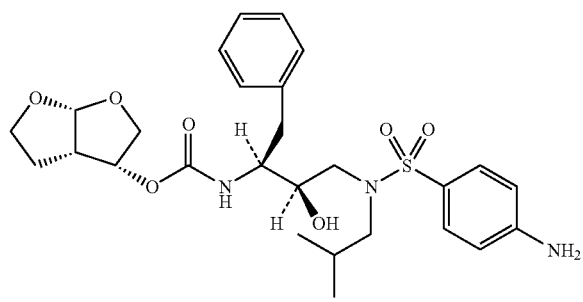

(I)

in which PG represents a protecting group and X represents a halogen atom.

Examples of the reaction of the above type involving the reaction of a secondary amine with a phenylsulfonyl halide derivative are described in EP 810209, EP885887 and WO 01/46120. In these publications such reactions are conventionally effected in a solvent system comprising an aprotic solvent such as toluene, dichloromethane or ethyl acetate. In addition to the solvent, an acid scavenger such as triethylamine is employed. For the isolation of the compound of formula (I) the work-up procedure usually includes a washing step followed by evaporation of the solvent and subsequent crystallisation of the product. A major disadvantage of this procedure is that the desired product of formula (I), especially when PG is a tertbutyloxycarbonyl group, has only a low solubility in most organic solvents. To enable a washing step to be performed the product must remain in solution. The choice of solvents is therefore determined by a) its suitability for use in the reaction and b) its need to be non-miscible with water, otherwise extraction cannot be performed. However, with the use of prior art solvents mentioned above it is necessary to use large volumes of solvent to ensure solubilisation of the product, which is disadvantageous for both economic and environmental reasons.

In contrast to the use of the above solvents we have now found a procedure in which the reaction is conducted in certain solvents which provide significant advantages over the former solvents. Thus we have found that the use of certain water-miscible solvents enables the product of formula (I) to be readily isolated in good yield and purity without the use of excessive volumes of solvent required in previous processes. In particular the use of a secondary or tertiary alcohol as solvent in the above reaction provides significant advantages described in more detail below.

According to the present invention therefore we provide a process for the preparation of N-isobutyl-N-(2-hydroxy-3-amino-4-phenylbutyl)-p-nitrobenzenesulfonylamide derivatives of formula (I) which comprises reacting a compound of formula (II) with a compound of formula (III) in a solvent comprising a secondary or tertiary alcohol:

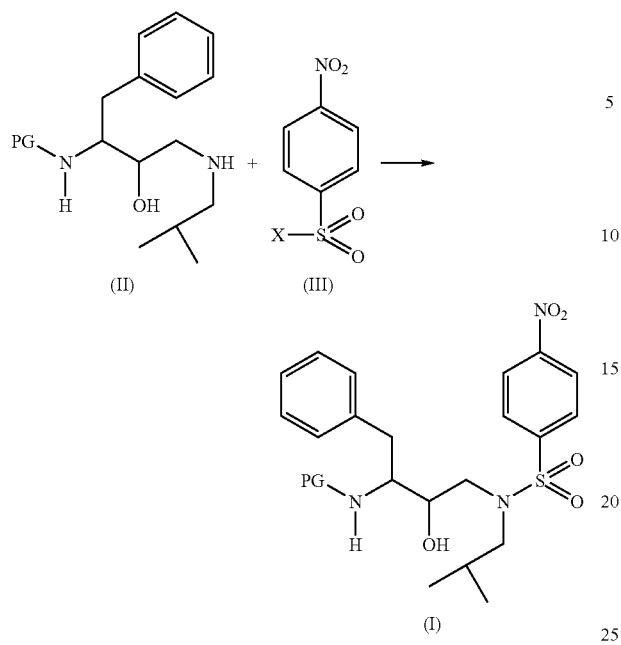

(II)  (III)  (I)

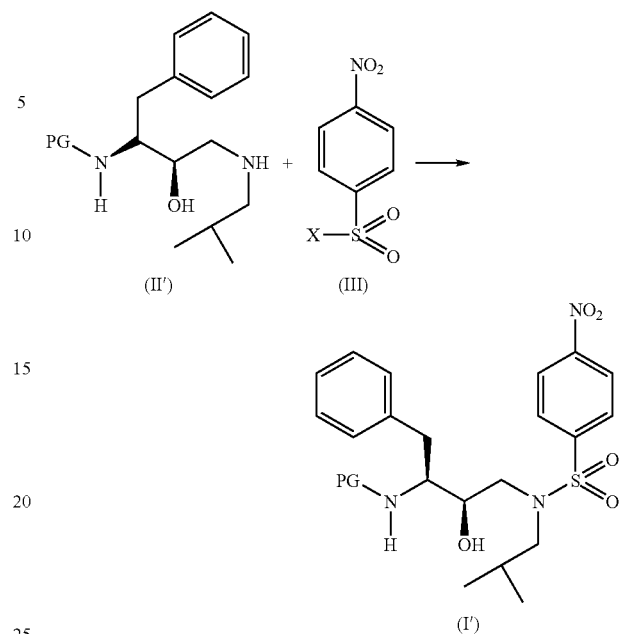

(II')  (III)  (I')

in which PG is a protecting group and X is a halogen atom.

In a preferred embodiment of the above process according to the invention the protecting group PG is advantageously an alkyl-, aryl- or arylalkyl-oxycarbonyl group, a $C_{1-4}$ alkyl group being preferred, especially the tert-butyloxycarbonyl group. The halogen atom X is preferably a chlorine atom.

The secondary or tertiary alcohol is preferably a $C_{1-5}$ alkanol for example a $C_{3-5}$alkanol such as 2-butanol, 2,2-dimethyl-1-propanol (neopentyl alcohol) or 2-methyl-2-butanol (tert-amyl alcohol) but especially a propanol, isopropanol being especially preferred. Alternatively tert-butanol can be advantageously used.

The reaction is generally performed in the presence of an acid scavenger such a tertiary amine base, triethylamine being especially preferred. Other suitable bases include N-methylmorpholine and diisopropylethylamine (Hunig's base), and also inorganic bases for example a phosphate base such as disodium hydrogen phosphate.

The reaction is generally performed at an elevated temperature for example 40 to 80° C. especially 50 to 70° C.

By the use of a secondary or tertiary alcohol as reaction solvent the desired product of formula (I) crystallises from solution, enabling it to be readily separated from the reaction mixture. Water is generally added subsequently to the reaction mixture to form a suspension with the organic reaction solvent to remove water-soluble reaction by-products or impurities such as acid addition salts formed by reaction of the acid scavenger and the halide compound of formula (III). The crystallised product can then be filtered off from the organic/water suspension and optionally purified for example by washing with a water/iso-propanol mixture.

In order to provide a compound of formula (I) having the (1S,2R) stereochemical configuration corresponding to darunavir above we provide the following preferred embodiment of the invention which comprises reacting a compound of formula (II') with a compound of formula (III) in a solvent comprising a secondary or tertiary alcohol to provide a compound of formula (I'):

In an especially preferred embodiment of the invention we provide a process for the preparation of a N-isobutyl-N-(2-hydroxy-3-amino-4-phenylbutyl)-p-nitrobenzene-sulfonylamide derivative of formula (I") which comprises reacting a compound of formula (II") with a compound of formula (III") in a solvent comprising a secondary or tertiary alcohol:

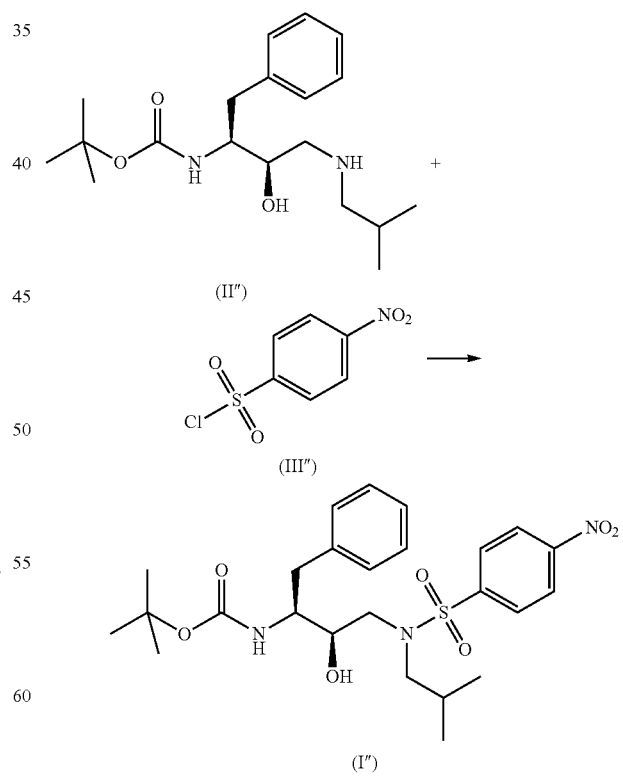

(II")  (III")  (I")

The resulting product of formula (I) can be obtained in high yield for example at least 90% and in very high purity for example at least 99%.

The term "alkyl" alone or in combination with any other term refers, except where otherwise specified, to straight-chain or branched-chain saturated aliphatic hydrocarbon radicals or, in the event that at least three carbon atoms are present, cyclic saturated aliphatic hydrocarbon radicals, containing 1 to 10 carbon atoms, preferably 1 to 8 carbon atoms, more preferably 1 to 6 carbon atoms or even more preferably 1 to 4 carbon atoms. Examples of such radicals include but are not limited to, methyl, ethyl, n-propyl, iso-propyl, n-butyl, iso-butyl, sec-butyl, tert-butyl, pentyl, iso-pentyl, n-hexyl, cyclopropyl, cyclobutyl, cyclopentyl, cyclohexyl and the like.

The term "aryl" alone or in combination with any other term, refers to a carbocyclic aromatic moiety and includes monocyclic, bicyclic and other polycyclic radicals. Examples of aryl radicals include but are not limited to phenyl and naphthyl radicals.

The term "halogen" refers to a fluorine, chlorine, bromine or iodine atom.

The present invention also includes the stereoisomeric forms of the compounds employed in the process according to the invention including starting materials and compounds subsequently prepared from compounds which are themselves prepared in accordance with the present invention.

The term "stereoisomeric forms" as used herein defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. Except where specified, all stereoisomeric forms of the compounds employed in the present invention both in pure form or in admixture with each other are intended to be embraced within the scope of the present invention.

Pure stereoisomeric forms of the compounds mentioned herein, i.e. where a particular stereoisomeric form is specified, are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds having a stereoisomeric excess of 90% up to 100%, even more in particular having a stereoisomeric excess of 94% up to 100% and most in particular having a stereoisomeric excess of 97% up to 100%.

Pure stereoisomeric forms of the compounds mentioned herein may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereoselectively. Preferably, if a specific stereoisomer is desired, said compound will be synthesized by stereoselective methods of preparation. These methods will advantageously employ enantiomerically pure starting materials.

The compounds of formula (II) can be prepared in conventional manner for example by methods described in the literature for example that described in WO 05/063770 including the synthesis described below.

Thus a compound of formula (II) can be prepared by introducing an isobutylamino group in a compound of formula (IV):

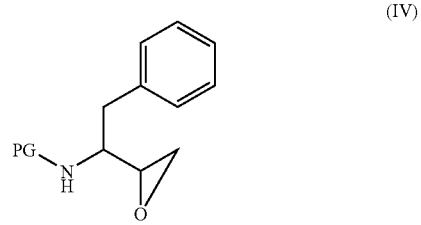

(IV)

to obtain a compound of formula (II).

For the preparation of a compound of formula (II') an isobutylamino group is introduced into a compound of formula (IV'):

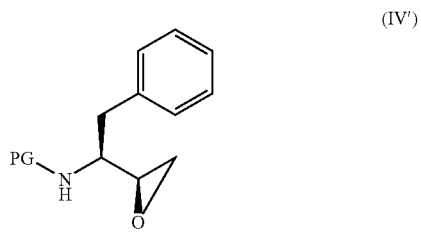

(IV')

Preferably the compound of formula (IV) is a compound of formula (IV") as shown below wherein PG is a tert-butyloxycarbonyl or "Boc" group. Compounds of formula (IV), (IV') and (IV") are commercially available and may be prepared in several ways available in the literature, for example as described in WO95/06030 (Searle & Co.), as described by Kaneka Corporation in EP0754669 EP1029856 and EP1067125, and as disclosed by Ajinomoto KK in EP1081133 and EP1215209.

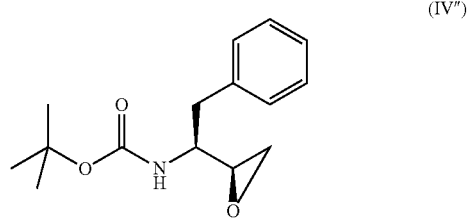

(IV")

The isobutyl amination of the compound of formula (IV) may be accomplished in several ways available in the literature, for example as described in WO95/06030, which is incorporated herein by reference.

In a preferred embodiment, the compound of formula (IV") is reacted with isobutylamine to yield the compound of formula (II").

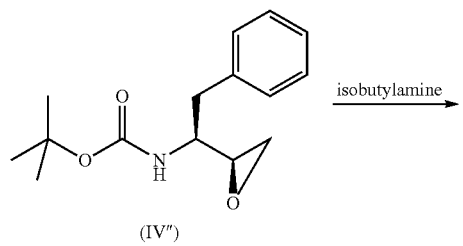

(IV")

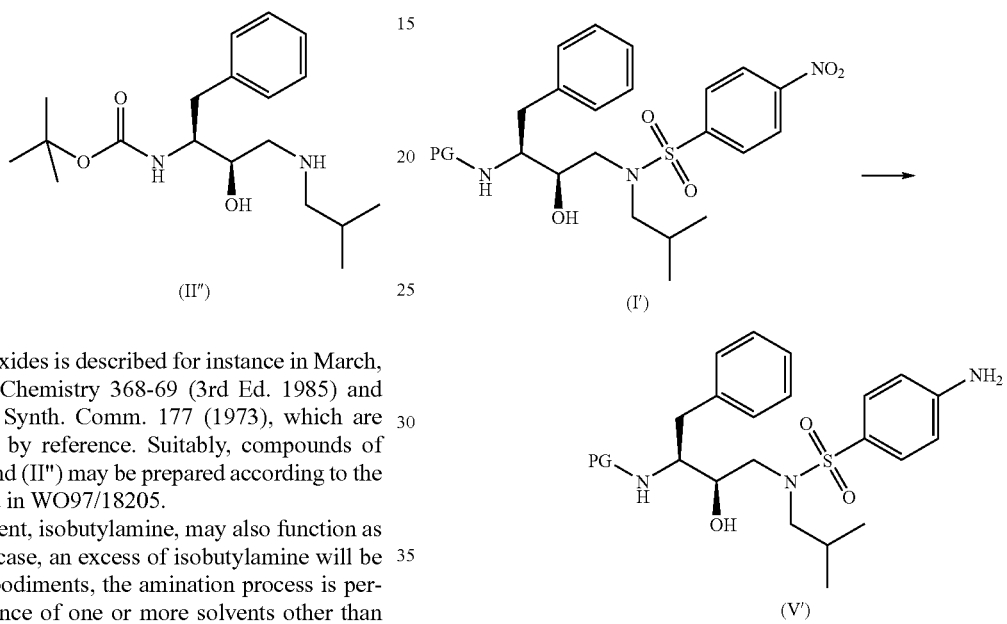

Amination of epoxides is described for instance in March, Advanced Organic Chemistry 368-69 (3rd Ed. 1985) and McManus et al., 3 Synth. Comm. 177 (1973), which are incorporated herein by reference. Suitably, compounds of formulae (II), (II') and (II") may be prepared according to the procedure described in WO97/18205.

The amination agent, isobutylamine, may also function as a solvent, in which case, an excess of isobutylamine will be added. In other embodiments, the amination process is performed in the presence of one or more solvents other than isobutylamine. In a preferred embodiment, said solvents are used in the work-up of compounds of formulae (II), (II') and (II").

In an embodiment of the invention, the amination reaction is carried out in the presence of about 15 equivalents of isobutylamine, using toluene as solvent, and heating to reflux at about 79° C.

The compounds of formula (I) and in particular the compounds of formulae (I') and (I") above are useful in the preparation of medicaments. According to a preferred embodiment, the compounds of formula (I) including the compounds of formulae (I') and (I") are used as precursors in the preparation of anti-viral drugs, in particular anti-HIV drugs, more in particular HIV protease inhibitors.

The compound of formula (I) and all intermediates leading to the formation of said compounds are of particular interest in preparing HIV protease inhibitors as disclosed in WO 99/65870, WO 99/67254, WO 99/67417, WO-00/47551, WO 00/76961, WO 05/063770 and EP 0 715 618. all incorporated herein by reference, and in particular, the HIV protease inhibitor: [(1S,2R)-3-[[(4-aminophenyl)sulfonyl]-(2-methylpropyl)amino]-2-hydroxy-1-(phenylmethyl)propyl]-carbamic acid (3R,3aS,6aR)-hexahydrofuro[2,3-b]furan-3-yl ester, namely darunavir referred to above.

Thus, the present invention also relates to the HIV protease inhibitor darunavir whenever obtained using a compound of formula (I), particularly a compound of formula (I') or (I"), prepared according to the present invention in the chemical synthesis of said HIV protease inhibitors. Such chemical synthesis is disclosed in the literature, for instance in the above patent and literature references.

The compounds of formulae (I) above, including compounds of formula (I') or (I"), can be used, after formation of an activated derivative, to synthesise the protease inhibitor darunavir of formula (A) above, as described for example in WO2005/063770, the contents of which are incorporated herein by reference.

For example the compound of formula (I') can be reduced to convert the nitro group to an amino group to form a compound of formula (V'):

Reducing agents suitable for reduction of the nitro moiety are metallic reducing reagents such as borane complexes, diborane, sodium borohydride, lithium borohydride, sodium borohydride-LiCl, aluminum lithium hydride, or diisobutyl-aluminium hydride; metals such as iron, zinc, tin and the like; and transition metals such as palladium-carbon, platinum oxide, Raney-nickel, rhodium, ruthenium and the like. When catalytic reduction is applied, ammonium formate, sodium dihydrogen-phosphate, hydrazine may be used as the hydrogen source.

According to a preferred embodiment of the invention a compound of formula (I") is reduced to form a compound of formula (V"):

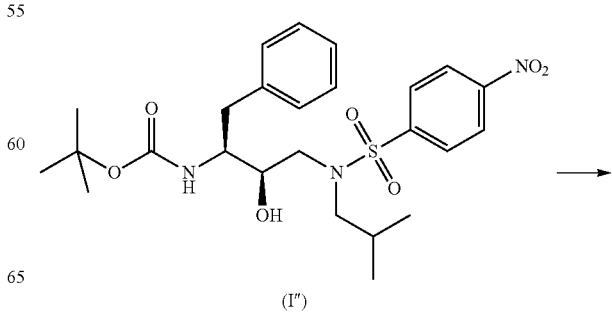

(I")

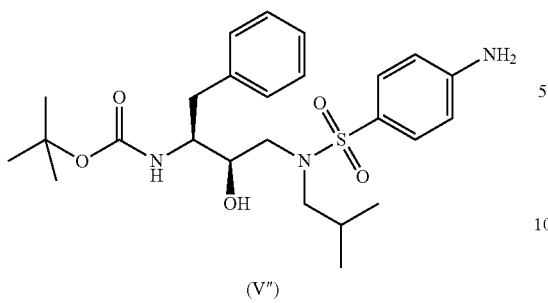

(V″)

The compound of formula (V') can then be deprotected to form a compound of formula (VI):

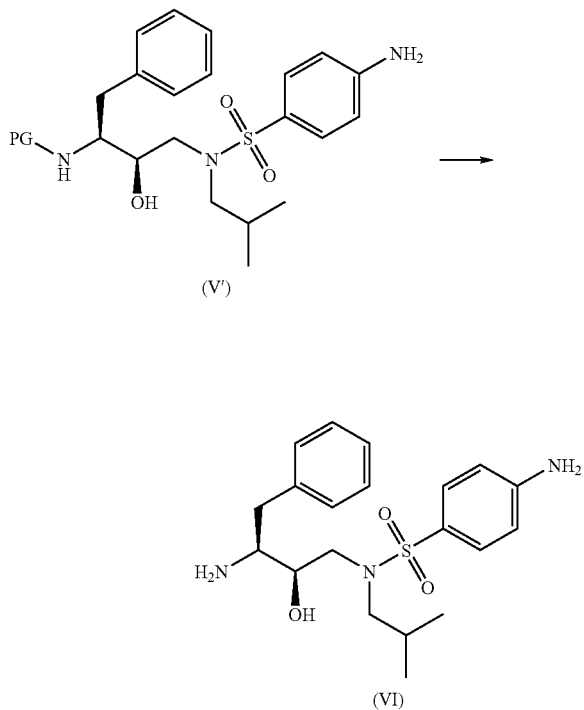

Removal of the amino-protecting-group can be achieved using conditions which will not affect the remaining portion of the molecule. These methods are well known in the art and include acid hydrolysis, hydrogenolysis and the like, thus using commonly known acids in suitable solvents.

Examples of reagents and methods for deprotecting amines from amino protecting groups can additionally be found in *Protective Groups in Organic Synthesis* by Theodora W. Greene, New York, John Wiley and Sons, Inc., 1981, incorporated herein by reference.

As those skilled in the art will recognize, the choice of amino protecting group employed in a previous step of the process will dictate the reagents and procedures used in removing said amino protecting group.

The compound of formula (VI) is then coupled with a hexahydrofuro[2,3-b]furan-3-yl derivative to obtain darunavir of formula (A). The hexahydrofuro[2,3-b]furan-3-yl derivative is advantageously an activated derivative of hexahydrofuro[2,3-b]furan-3-ol of formula (VII):

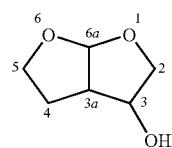

and in particular an activated derivative of (3R,3aS,6aR)-hexahydrofuro[2,3-b]furan-3-ol of formula (VII'):

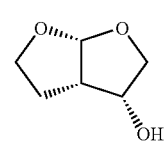

The compound of formula (VII) above can be prepared in conventional manner for example as described in WO 03/022853, US 2004/0162340, WO 2004/033462, U.S. Pat. No. 6,867,321, WO-2005/095410 and also Ghosh et al, J. Org. Chem. 2004, 69, 7822-7829.

The compound of formula (VII) is suitably activated with a coupling agent to generate a hexahydrofuro[2,3-b]furan-3-yl derivative which is then carbamoylated with the compound of formula (VI) to obtain the protease inhibitor darunavir.

Examples of coupling agents used in carbamoylation reactions are carbonates such as bis-(4-nitrophenyl)carbonate, disuccinimidyl carbonate (DSC), carbonyl diimidazole (CDI). Other coupling agents include chloroformates, such as p-nitrophenylchloroformate, phosgenes such as phosgene and triphosgene.

In particular, when (3R,3aS,6aR)-hexahydrofuro[2,3-b]furan-3-ol is reacted with disuccinimidyl carbonate, 1-([[[(3R,3aS,6aR)hexahydrofuro[2,3-b]furan-3-yloxy]-carbonyl]oxy)-2,5-pyrrolidinedione is obtained. Said compound is a preferred (3R,3aS,6aR)-hexahydrofuro[2,3-b]furan-3-yl derivative:

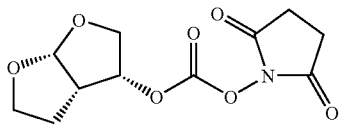

Reaction of the (3R,3aS,6aR)-hexahydrofuro[2,3-b]furan-3-yl derivative with the compound of formula (VI) will be performed in the presence of suitable solvents, such as tetrahydrofuran, dimethylformamide, acetonitrile, dioxane, dichloromethane or chloroform, and optionally with bases, such as triethylamine although further combinations from the solvents and bases hereinabove disclosed are also embodied. Among the solvents, preferred solvents are aprotic solvents such as tetrahydrofuran, acetonitrile, dimethylformamide, ethyl acetate, and the like.

The above carbamoylation reaction is suitably carried out at a temperature between −70° C. and 40° C., preferably between −10° C. and 20° C.

Accordingly to a particularly preferred feature of the present invention we provide darunavir, namely [(1S,2R)-3-[[(4-aminophenyl)sulfonyl](2-methylpropyl)amino]-2-hydroxy-1-(phenylmethyl)propyl]-carbamic acid (3R,3aS,6aR)-hexahydrofuro-[2,3-b]furan-3-yl ester of formula (A), whenever synthesised using an intermediate of formula (I), including an intermediate of formula (I'), prepared in accordance with the present invention.

The following Example is illustrative of the present invention. The Example is presented to exemplify the invention and are not to be construed as limiting the scope of the invention.

EXAMPLE 7.5 g (22.3 mmol) of (1S,2R)-(1-benzyl-2-hydroxy-3-isobutylamino-propyl)-carbamic acid tert-butyl ester and 2.7 g (26.8 mmol, 1.2 equiv) of triethylamine are dissolved in 100 g of isopropanol and heated to 60-65° C. 5.41 g (24.5 mmol, 1.1 eq) p-nitrophenyl-sulfonyl chloride are added in several portions within 30 minutes. The reaction mixture is kept at 60° C. for another 30 minutes. 10 g of water are added and the suspension is stirred for an additional 30 minutes at 60° C. The mixture is cooled to 25° C. within 90 min and the product is filtered off, washed with a mixture of isopropanol/water (1:1 v/v) and dried under vacuum to yield 11.23 g (96.5%) of white (1S,2R)-{1-benzyl-2-hydroxy-3-[isobutyl-(4-nitrobenzenesulfonyl)-amino]-propyl}-carbamic acid tert-butyl ester.

HPLC purity >99.8%, no single impurity >0.05%.

The invention claimed is:

1. A process for the preparation of N-isobutyl-N-(2-hydroxy-3-amino-4-phenylbutyl)-p-nitrobenzenesulfonylamide derivatives of formula (I) which comprises reacting a compound of formula (II) with a compound of formula (III) in a water-miscible solvent comprising a secondary or tertiary alcohol:

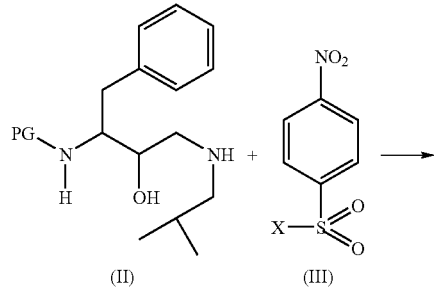

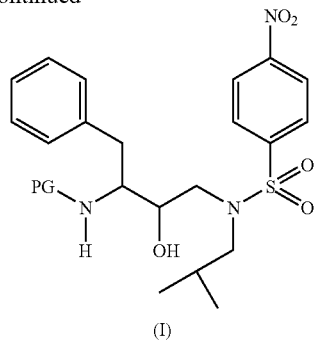

in which PG is a protecting group and X is a halogen atom.

2. A process as claimed in claim 1 in which the secondary or tertiary alcohol is a $C_{3-5}$ alcohol.

3. A process as claimed in claim 2 in which the secondary or tertiary alcohol is isopropanol.

4. A process as claimed in claim 1 in which the PG protecting group is a $C_{1-4}$ alkyloxycarbonyl group.

5. A process as claimed in claim 4 in which the PG protecting group is a tert-butyloxycarbonyl group.

6. A process as claimed in claim 1 in which the halogen atom X is a chlorine atom.

7. A process as claimed in claim 1 in which the reaction is performed in the presence of an acid scavenger.

8. A process as claimed in claim 7 in which the acid scavenger is triethylamine.

9. A process as claimed in claim 1 in which the reaction is performed at a temperature of 50 to 70° C.

* * * * *